United States Patent [19]

Denzel et al.

[11] 4,109,087
[45] Aug. 22, 1978

[54] 1,4- AND 4,10-DIHYDRO-4-OXO-PYRIMIDO[1,2-a]BENZIMIDAZOLE-3-CARBOXYLIC ACID AMIDES

[75] Inventors: Theodor Denzel, Regensburg; Hans Hoehn, Tegernheim, both of Fed. Rep. of Germany

[73] Assignee: E. R. Squibb & Sons, Inc., Princeton, N.J.

[21] Appl. No.: 860,021

[22] Filed: Dec. 12, 1977

Related U.S. Application Data

[63] Continuation-in-part of Ser. No. 696,329, Jun. 15, 1976, Pat. No. 4,072,679.

[51] Int. Cl.² .......................................... C07D 487/04
[52] U.S. Cl. .................................... 544/115; 544/58; 544/250; 424/246; 424/248.54
[58] Field of Search ........................... 544/115, 58; 260/256.4 F

[56] References Cited

U.S. PATENT DOCUMENTS 3,468,888  9/1969  Chow ........................... 260/256.4 F

*Primary Examiner*—Henry R. Jiles
*Assistant Examiner*—R. W. Ramsuer
*Attorney, Agent, or Firm*—Lawrence S. Levinson; Merle J. Smith

[57] ABSTRACT

New 1,4- and 4,10-dihydro-4-oxo-pyrimido[1,2-a]-benzimidazole-3-carboxamides have the general formulas

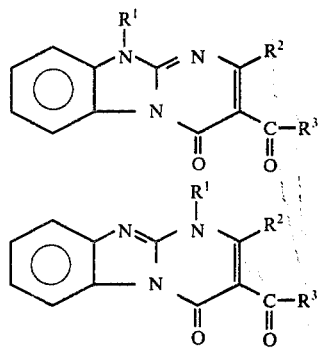

They are useful as central nervous system depressants and anti-inflammatory agents.

12 Claims, No Drawings

1,4- AND 4,10-DIHYDRO-4-OXO-PYRIMIDO[1,2-A]BENZIMIDAZOLE-3-CARBOXYLIC ACID AMIDES

This application is a continuation-in-part of application Ser. No. 696,329, filed June 15, 1976, now U.S. Pat. No. 4,072,679.

SUMMARY OF THE INVENTION

This invention relates to new carboxylic acids, esters and carboxamides of 1,4- and 4,10-dihydro-4-oxopyrimido[1,2-a]benzimidazole, as well as their salts. These new compounds have the general formulas

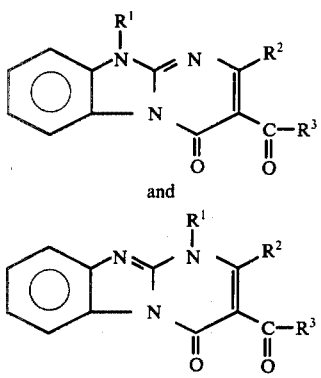

The symbols have the following meanings in the formulas I, II and throughout this specification.

$R^1$ is hydrogen, lower alkyl, phenyl-lower alkyl, di-lower alkylamino-lower alkyl, i.e.,

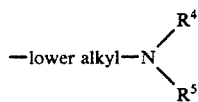

wherein $R^4$ and $R^5$ each is lower alkyl. The basic group

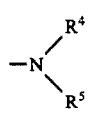

may also form an unsubstituted or substituted heterocycle

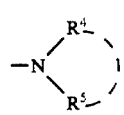

in which $R^4$ and $R^5$ join with the nitrogen to complete one of the heterocyclic groups, piperidino, piperazinyl, morpholino, thiamorpholino, each of which may also bear as a substituent a hydroxy-lower alkyl group or one or two lower alkyl groups.

$R^2$ is hydrogen or lower alkyl.

$R^3$ is hydroxy, lower alkoxy or an amino group

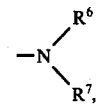

wherein $R^6$ and $R^7$ each is hydrogen, lower alkyl, phenyl, substituted phenyl, (wherein the phenyl substituent is halo, lower alkyl or lower alkoxy), phenyl-lower alkyl or di-lower alkylamino-lower alkyl group like the one described above for $R^1$. The basic group

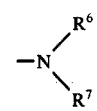

may also form an unsubstituted or substitued heterocycle of 5 or 6 members,

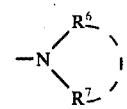

in which $R^6$ and $R^7$ join with the nitrogen to complete a heterocyclic group in which an additional hetero atom is present, i.e., pyrrolidino, piperidino, piperazinyl, morpholino, thiamorpholino, each of which may bear as a substituent a hydroxy-lower alkyl group or one or two lower alkyl groups.

DETAILED DESCRIPTION OF THE INVENTION

The groups represented by the symbols have the following meanings throughout this specification.

The lower alkyl groups are straight or branched chain hydrocarbon groups in the series from methyl to heptyl having up to seven carbons, like methyl, ethyl, propyl, isopropyl, butyl, isobutyl, t-butyl and the like. The $C_1$–$C_4$ members are preferred and the $C_1$–$C_2$ members are especially preferred.

The lower alkoxy groups include similar alkyl groups to which an oxygen is attached. The same $C_1$–$C_4$ and $C_1$–$C_2$ preferences apply.

The phenyl-lower alkyl groups include similar alkyl groups to which a phenyl ring is attached. The phenyl-($C_1$–$C_4$) lower alkyl and phenyl-($C_1$–$C_2$) lower alkyl groups similarly constitute preferred and especially preferred groups.

The substituted phenyl groups include such radicals as halophenyl, e.g., o-, m- or p-chlorophenyl, o-, m- or p-bromophenyl, etc., o-, m- or p-tolyl, o-, m- or p-methoxyphenyl and the like.

The halogens are the four common halogens, chlorine and bromine being preferred, especially the first.

The amino groups represented by the radical

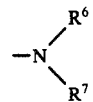

include amino, lower alkylamino groups like methylamino, ethylamino, propylamino, isopropylamino, etc., or di-(lower alkyl) amino groups like dimethylamino, diethylamino, dipropylamino, methylethylamino and the like, or groups like anilino, phenylmethylamino, phenylethylamino, p-methoxyphenylamino, etc. A di-lower alkylamino-lower alkyl group may also be present on the nitrogen forming such groups as dimethyl aminomethylamino, dimethylaminoethylamino, diethylaminomethylamino, diethylaminoethylamino, dipropylaminoethylamino, methyl(ethyl)aminoethylamino, and the like. The di-lower alkylamino-lower alkyl groups represented by $R^1$ are similar groups with but one nitrogen. The lower alkyl groups in each of the foregoing radicals is preferably $C_1$-$C_4$ and $C_1$-$C_2$ as described above. Preferably also the $$-N\begin{matrix}R^6\\R^7\end{matrix}$$

group includes only one phenyl, substituted phenyl, phenyl-lower alkyl or di-lower alkylamino-lower alkyl group, i.e., $R^6$ is phenyl, substituted phenyl, phenyl-lower alkyl or di-lower alkylamino-lower alkyl and $R^7$ is then hydrogen. In addition, in any of the di-lower alkyl groups, preferably but not necessarily, both lower alkyl groups in a given compound are the same.

The $$-N\begin{matrix}R^4\\R^5\end{matrix}$$

group and $$-N\begin{matrix}R^6\\R^7\end{matrix}$$

can also represent a heterocyclic radical of the group described wherein the R's join to complete the heterocycle, e.g., piperidino, pyrrolidino, piperazinyl, lower alkylpiperidino, e.g., 2-, 3- or 4-methylpiperidino, (preferably 4-methylpiperidino), 2-, 3- or 4-ethylpiperidino, etc., lower alkylpiperazinyl, e.g., 4-methylpiperazin-1-yl (which is preferred), 4-ethyl-piperazin-1-yl, etc., or (hydroxy-lower alkyl)piperazinyl, e.g., 4-hydroxyethylpiperazin-1-yl, and the like.

The products of the examples, which are representative of the various compounds of this invention, constitute preferred embodiments. Especially preferred compounds of the formulas I and II are those wherein $R^1$ is lower alkyl, especially ethyl, $R^2$ is lower alkyl or hydrogen, especially hydrogen, $R^3$ is hydroxy, lower alkoxy, lower alkylamino, especially butylamino.

The new isomeric compounds of the formulas I and II are formed by the following series of reactions. The symbols in the structural formulas have the same meaning as previously described.

An alkoxymethylenemalonic acid ester of the formula $$\text{lower alkyl}-O-C=C\begin{matrix}COO-\text{lower alkyl}\\R^2\end{matrix}\begin{matrix}\\COO-\text{lower alkyl}\end{matrix} \quad (III)$$

is made to react with a 2-aminobenzimidazole of the formula (IV)

The reaction is accomplished at 120°–130° in a solvent like dimethylformamide, acetic acid, or the like. A product of the formula (V)

is formed. This compound is now alkylated with an alkyl halide $R^1$-hal, wherein hal represents halogen, preferably iodine, chlorine or bromine, in a solvent like dimethylformamide and in the presence of a base like potassium carbonate or the like, at about 80° C over a period of 2 to 3 days. This reaction results in the formation of a mixture of the isomeric compounds of formulas Ia and IIa:

(Ia)

and (IIa)

These isomeric products can be separated by repeated crystallization from acetone, dimethylformamide or the like or by chromatography on silica gel, alumina or the like. Compounds of the formula Ia are more soluble in the acetone, dimethylformamide, etc.

Compounds of the formula (Ib)

and compounds of the formula

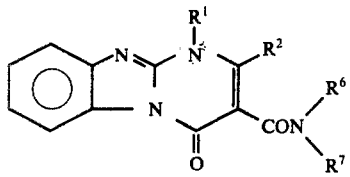  (IIb)

with a carboxamide function are obtained by treating the compound of formula Ia or IIa, respectively, with an appropriately substituted amine of the formula

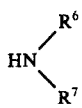  (VI)

The reaction proceeds at a temperature of about 80° to 120° C. Sometimes, when low boiling amines are used, the reaction is run in an autoclave.

In an alternative procedure, compounds of formulas Ib or IIb are obtained by treatment of a compound of formulas Ia or IIa, respectively, with a base like potassium hydroxide or sodium hydroxide in aqueous methanol. By this reaction an acid of the formula

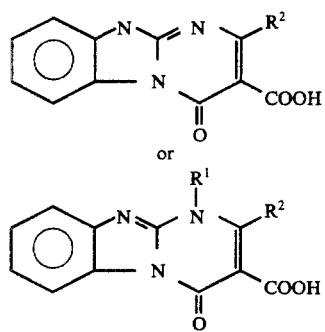

is obtained. The acid is refluxed with an inorganic acid chloride like phosphorus oxychloride or thionyl chloride. An acid chloride of the formula

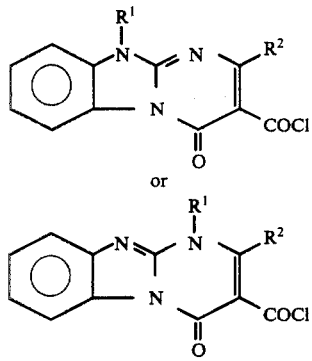

is formed. The compound of formula Ib or IIb is now obtained by reaction of the compound of formulas Id or IId with the amine of formula VI.

The new compounds of formula I form salts which are also part of this invention. The salts include acid addition salts, particularly the non-toxic, physiologically acceptable members. These salts are formed by reaction with one or more equivalents of any of a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate or aryl- or alkanesulfonates like benzene-sulfonate, methanesulfonate and toluenesulfonate, or cyclohexanesulfamate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with one or more equivalents of acid containing the desired anion.

Additional experimental details are found in the examples.

The new compounds of this invention are central nervous system depressants which can be used as psychotropic agents, e.g., as ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 2 to 15 mg. per kilogram per day, is recommended.

The new compounds of this invention also have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg. per kilogram per day, preferably 5 to 25 mg. per kilogram per day, in single or 2 to 4 divided doses, as indicated by the carageenan edema assay or delayed hypersensitivity reaction test in rats.

The compounds of the invention can be utilized by formulating in compositions such as tablets, capsules or elixirs for oral administration or in sterile solutions or suspensions for parenteral administration. About 10 to 300 mg. of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. They also serve as models for the preparation of other members of the group which can be produced by suitable substitution of starting materials. All temperatures are in degrees celsius.

EXAMPLE 1

10-Ethyl-4,10-dihydro-4-oxo-pyrimido[1,2-a]benzimidazole-3-carboxylic acid, ethyl ester and 1-Ethyl-1,4-dihydro-4-oxopyrimido[1,2-a]benzimidazole-3-carboxylic acid, ethyl ester (a)
4-Hydroxypyrimido[1,2-a]benzimidazole-3-carboxylic acid, ethyl ester 266 g. of 2-aminobenzimidazole (2 mol.) and 432 g. of ethoxymethylene malonic acid diethyl ester are heated with stirring in 3 liters of DMF at 80° for 3 hours. The solution is cooled to room temperature and then filtered off and the crystalline 4-hydroxypyrimido[1,2-a]-benzimidazole-3-carboxylic acid, ethyl ester is recrystallized from acetic acid, yield 490 g. (95%); m.p. 309°-310°.

(b)
10-Ethyl-4,10-dihydro-4-oxo-pyrimido[1,2-a]benzimidazole-3-carboxylic acid, ethyl ester and 1-Ethyl-1,4-dihydro-4-oxo-pyrimido[1,2-a]benzimidazole-3-carboxylic acid, ethyl ester 257 g. of 4-hydroxypyrimido[1,2-a]benzimidazole-3-carboxylic acid, ethyl ester (1 mol.), 204.5 g. of ethyl iodide (1.3 mol.) and 182 g. of potassium carbonate are heated in 1.5 liters of DMF with stirring at 80° for 72 hours. The insoluble inorganic material is removed by filtration and about 1 liter of water is added to the filtrate. A mixture of the two title compounds crystallizes and is filtered off and dried at 60°. The crystalline mixture is now dissolved in hot acetone and allowed to stand until the temperature reaches about 22°. The precipitated 1-ethyl-1,4-dihydro-4-oxo-pyrimido[1,2-a]-benzimidazole-3-carboxylic acid, ethyl ester is filtered off and recrystallized from acetone, yield 99 g. (35%); m.p. 211°-213°.

The mother liquors are combined, evaporated to dryness and dissolved in hot acetone. The solution is cooled to about 20° and allowed to stand for 1 hour. A mixture of the two compounds is obtained (about 12 g.) and filtered off. The filtrate is cooled in an ice bath and the precipitated 10-ethyl-4,10-dihydro-4-oxo-pyrimido[1,2-a]-benzimidazole-3-carboxylic acid, ethyl ester is filtered off (purity about 90%); m.p. 158°-160°; yield 92 g. (32%). This compound is pure enough for further reactions. For further purification, the compound is recrystallized about 3 times from hot acetone until the melting point has reached 160°-161°.

By following the above procedure, substituting for the ethyl iodide in part (b) the indicated alkyl halide, the following products are obtained:

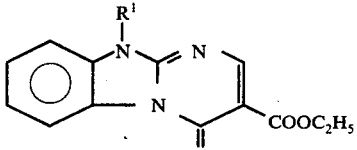

A

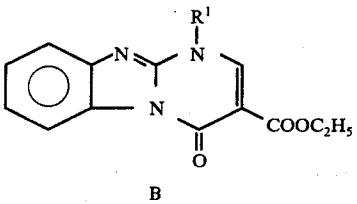

B

| Example | Compound | Alkylhalide | R¹ | m-p |
|---|---|---|---|---|
| 2 | A | BrCH$_2$CH$_2$CH(CH$_3$)$_2$ | —CH$_2$CH$_2$CH(CH$_3$)$_2$ | 123-125° |
| 2 | B | BrCH$_2$CH$_2$CH(CH$_3$)$_2$ | —CH$_2$CH$_2$CH(CH$_3$)$_2$ | 134-136 |
| 3 | A | BrC$_3$H$_7$ | —C$_3$H$_7$ | 155-158 |
| 3 | B | BrC$_3$H$_7$ | —C$_3$H$_7$ | 158-161 |
| 4 | A | ICH$_3$ | —CH$_3$ | 172-175 |
| 4 | B | ICH$_3$ | —CH$_3$ | 233-235 |
| 5 | A | BrCH$_2$—C$_6$H$_5$ | —CH$_2$—C$_6$H$_5$ | 188-190 |
| 5 | B | BrCH$_2$—C$_6$H$_5$ | —CH$_2$—C$_6$H$_5$ | 186-187 |
| 6 | A | ClCH$_2$CH$_2$CH$_2$N(CH$_3$)$_2$ | —(CH$_2$)$_3$N(CH$_3$)$_2$ | 142-143 |
| 6 | B | ClCH$_2$CH$_2$CH$_2$N(CH$_3$)$_2$ | —(CH$_2$)$_3$N(CH$_3$)$_2$ | 125-126 |

EXAMPLE 7

N-Butyl-10-ethyl-4,10-dihydro-4-oxo-pyrimido[1,2-a]benzimidazole-3-carboxamide 8 g. of 90% pure 10-ethyl-4,10-dihydro-4-oxo-pyrimido-[1,2-a]benzimidazole-3-carboxylic acid, ethyl ester produced as in Example 1b are refluxed with stirring in 30 ml. of n-butylamine for 12 hours. The solution is allowed to cool to room temperature. A small amount of precipitated isomeric N-butyl-1-ethyl-1,4-dihydro-4-oxo-pyrimido[1,2-a]benzimidazole-3-carboxamide (m.p. 232°-234°) is filtered off and the mother liquor evaporated to dryness. The remaining N-butyl-10-ethyl-4,10-dihydro-4-oxo-pyrimido[1,2-a]benzimidazole-3-carboxamide is recrystallized from ethyl acetate, m.p. 118°-120°, yield 6.5 g. (74%).

The hydrochloride salt is produced by treating the above product with ethanolic HCl and recrystallizing from propylene glycol, m.p. 124°-126°.

By following the above procedure of Example 7, substituting for the butylamine the indicated amine, the following additional products are obtained:

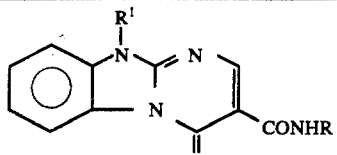

| Example | R¹ | Amine | R | m.p. | Yield |
|---|---|---|---|---|---|
| 8 | $CH_2CH_2CH(CH_3)_2$ | $H_2NC_4H_9$ | $-C_4H_9$ | 112–123° | 77% |
| 9 | $C_2H_5$ | $H_2NCH(CH_3)C_2H_5$ | $-CH(CH_3)C_2H_5$ | 108–110 | 68% |
| 10 | $CH_3$ | $H_2NC_4H_9$ | $-C_4H_9$ | 175–177 | 81% |
| 11 | $C_3H_7$ | $H_2NC_4H_9$ | $-C_4H_9$ | 211–212 | 69% |
| 12 | $C_2H_5$ | $H_2N(CH_2)_3N\diagup\diagdown O$ | $-(CH_2)_3N\diagup\diagdown O$ | 115–117 | 80% |
| 13 | $C_2H_5$ | $H_2N(CH_2)_3N(CH_3)_2$ | $-(CH_2)_3N(CH_3)_2$ | 80–82 | 71% |

The compounds of Examples 8–13 are recrystallized from ethyl acetate. The isomeric 1-substituted compound is obtained from the mother liquor.

EXAMPLE 14

N-Butyl-1-ethyl-1,4-dihydro-4-oxo-pyrimido[1,2-a]benzimidazole-3-carboxamide 10 g. of 1-ethyl-1,4-dihydro-4-oxo-pyrimido[1,2-a]-benzimidazole-3-carboxylic acid, ethyl ester obtained as in Example 1b are refluxed with 50 ml. of n-butylamine for 12 hours with stirring. The N-butyl-1-ethyl-1,4-dihydro-4-oxo-pyrimido[1,2-a]benzimidazole-3-carboxamide is filtered off after cooling, yield 8.3 g. (76%); m.p. 232°–234° (DMF/H₂O).

By following the above procedure of Example 14 substituting for the butylamine the indicated amine, the following additional products are obtained:

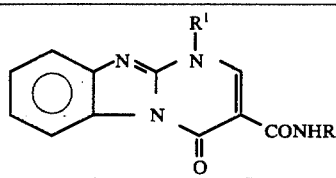

| Example | R¹ | Amine | R | m.p. | yield |
|---|---|---|---|---|---|
| 15 | $CH_3$ | $H_2NC_4H_9$ | $-C_4H_9$ | 266–267° | 88% |
| 16 | $C_2H_5$ | $H_2NCH(CH_3)C_2H_5$ | $-CH(CH_3)C_2H_5$ | 260–261 | 85% |
| 17 | $C_3H_7$ | $H_2NC_4H_9$ | $-C_4H_9$ | 219–221 | 81% |
| 18 | 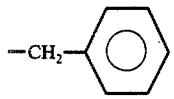 | $H_2NC_4H_9$ | $-C_4H_9$ | 242–213 | 75% |

The compounds of Examples 15–18 are recrystallized from DMF.

EXAMPLE 19

10-Ethyl-4,10-dihydro-N-methyl-4-oxo-pyrimido[1,2-a]benzimidazole-3-carboxamide 10 g. of 90% pure 10-ethyl-4,10-dihydro-4-oxo-pyrimido[1,2-a]-benzimidazole-3-carboxylic acid, ethyl ester produced in Example 1b are dissolved in 50 ml. of alcohol. After addition of 10 ml. of methylamine, the solution is heated in an autoclave at 100° for 12 hours. After this time, the solvent is distilled off and the crystalline residue is heated with hot acetone. The small amount of isomeric 1-ethyl-1,4-dihydro-N-methyl-4-oxo-pyrimido[1,2-a]benzimidazole-3-carboxamide is insoluble and is filtered off. After addition of water to the mother liquor, the 10-ethyl-4,10-dihydro-N-methyl-4-oxo-pyrimido-[1,2-a]benzimidazole-3-carboxamide crystallizes, yield 63%; m.p. 178°–180° (acetone).

By following the above procedure of Example 19, the following additional products are obtained:

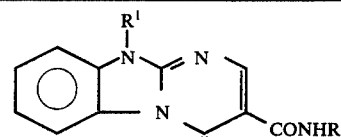

| Example | R¹ | Amine | R | m.p. | Yield |
|---|---|---|---|---|---|
| 20 | $CH_3$ | $H_2NCH_3$ | $-CH_3$ | 180–182° (DMF) | 68% |
| 21 | $-CH_2-\bigcirc$ | $H_2NCH_3$ | $-CH_3$ | 165–167 (DMF) | 70% |

EXAMPLE 22

1-Ethyl-1,4-dihydro-N-methyl-4-oxo-pyrimido[1,2-a]benzimidazole-3-carboxamide 10 g. of 1-ethyl-1,4-dihydro-4-oxo-pyrimido[1,2-a]benzimidazole-3-carboxylic acid, ethyl ester produced as in Example 1b are heated at 120° in butyl alcohol with 10 ml. of methylamine in an autoclave for 12 hours. The solvent is distilled off and the residue recrystallized from DMF, yield 88%; m.p. 270°–272°.

The following products are obtained by the procedure of Example 22:

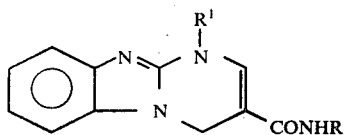

| Example | R¹ | Amine | R | m.p. | Yield |
|---|---|---|---|---|---|
| 23 | CH₃ | H₂NCH₃ | CH₃ | 325–326° (DMF) | 65% |
| 24 | —CH₂—⌬ | H₂NCH₃ | CH₃ | 280–283 (DMF) | 71% |

EXAMPLE 25

10-Ethyl-3-[(4-morpholinyl)carbonyl]pyrimido[1,2-a]benzimidazole-4(10H)-one (a)
10-Ethyl-4,10-dihydro-4-oxo-pyrimido[1,2-a]benzimidazole-3-carboxylic acid 28.5 g. of pure 10-ethyl-4,10-dihydro-4-oxo-pyrimido-[1,2-a]benzimidazole-3-carboxylic acid, ethyl ester produced as in Example 1b are stirred in a solution of 7 g. of potassium hydroxide in 200 ml. of alcohol for 15 hours at room temperature. After this time, the solvent is distilled in vacuo and the residue dissolved in 200 ml. of water and acidified with acetic acid. 10-ethyl-4,10-dihydro-4-oxo-pyrimido[1,2-a]benzimidazole-3-carboxylic acid precipitates and is filtered off, yield 20 g. (79%); m.p. 228°–230° (DMF).

(b)
10-Ethyl-3-[(4-morpholinyl)carbonyl]pyrimido[1,2-a]benzimidazole-4(10H)-one 2.6 g. of 10-ethyl-4,10-dihydro-4-oxo-pyrimido[1,2-a]-benzimidazole-3-carboxylic acid is refluxed with stirring in 20 ml. of thionyl chloride. The excess thionyl chloride is distilled off, the remaining residue treated with 10 ml. of toluene and again evaporated to dryness. The crystalline acid chloride is now suspended in 20 ml. of toluene and 2 g. of morpholine are added and the reaction mixture is stirred overnight. After evaporation of the solvent, the residue is treated with 10 ml. of water and filtered off. Recrystallization from ethyl acetate yields 2.5 g. of 10-ethyl-3-[(4-morpholinyl)-carbonyl]-pyrimido[1,2-a]benzimidazole-4(10H)-one; m.p. 200°–202°.

By following the above procedure of Example 26, substituting the appropriate amine, the following additional products are obtained:

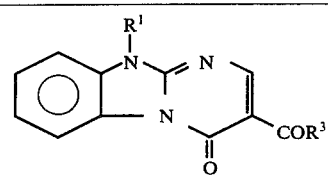

| Example | R¹ | R³ | m.p. | Yield |
|---|---|---|---|---|
| 26a | CH₃ | —OH | | |
| 26b | CH₃ | —N⌬N—CH₃ | 213–216° (ethylacetate) | 59% |

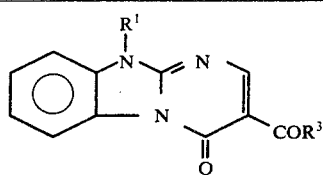

| Example | R¹ | R³ | m.p. | Yield |
|---|---|---|---|---|
| 27 | CH₃ | —N⌬O | 288–290 (DMF/H₂O) | 63% |
| 28 | C₂H₅ | —N⌬ | 188–190 (ethylacetate) | 72% |
| 29 | C₂H₅ | —N⌬N—CH₃ | 145–147 (ethylacetate) | 70% |
| 30 | C₂H₅ | —NH—⌬ | 180–182 (ethylacetate) | 73% |
| 31 | —CH₂—⌬ | —N⌬O | 241–242 (DMF) | 68% |
| 32 | —CH₂—⌬ | —N⌬N—CH₃ | 203–205 (DMF) | 65% |

EXAMPLE 33

1-Ethyl-1,4-dihydro-4-oxo-N-phenyl-pyrimido[1,2-a]benzimidazole-3-carboxamide (a)
1-Ethyl-1,4-dihydro-4-oxo-pyrimido[1,2-a]benzimidazole-3-carboxylic acid 28.5 g. of 1-ethyl-1,4-dihydro-4-oxo-pyrimido[1,2-a]-benzimidazole-3-carboxylic acid, ethyl ester produced as in Example 1b are heated with stirring in a solution of 7 g. of potassium hydroxide in 200 ml. of alcohol for 15 hours at 80°. The solvent is removed in vacuo and the residue dissolved in 200 ml. of water and acidified with acetic acid. 1-Ethyl-1,4-dihydro-4-oxo-pyrimido[1,2-a]benzimidazole-3-carboxylic acid precipitates and is filtered off, yield 81%; m.p. 252°–253°.

(b)
1-Ethyl-1,4-dihydro-4-oxo-N-phenyl-pyrimido[1,2-a]-benzimidazole-3-carboxamide 0.05 mol. of 1-ethyl-1,4-dihydro-4-oxo-pyrimido-[1,2-a]benzimidazole-3-carboxylic acid is refluxed with stirring in 100 ml. of thionyl chloride. After this time, the chlorinating agent is removed by distillation, the remaining acid chloride is treated with 50 ml. of toluene and again evaporated to dryness. After addition of 100 ml. of toluene, 0.1 mol. of aniline are added and the solution is stirred overnight. The solvent is distilled off and the residue treated with water and filtered. The product 1-ethyl-1,4-dihydro-4-oxo-N-phenyl-pyrimido[1,2-a]benzimidazole-3-carboxamide, is recrystallized from DMF, yield 73%; m.p. 268°–270°.

According to the foregoing procedure the following additional products are obtained:

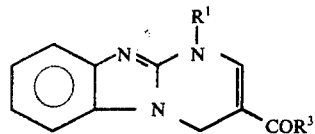

| Example | R¹ | R³ | m.p. | Yield |
|---|---|---|---|---|
| 34 | $C_2H_5$ | —N\_\_\_N—CH₃ (piperazine) | 178–180 (ethyl acetate) | 75% |
| 35 | $C_2H_5$ | —N\_\_\_ (piperidine) | 186–188 (ethyl acetate) | 78% |
| 36 | $CH_3$ | —N\_\_\_N—CH₃ (piperazine) | 220–221 (ethyl acetate) | 83% |
| 36A | $CH_3$ | —OH | 237–239 (DMF) | 80% |
| 37 | $CH_3$ | —N\_\_\_O (morpholine) | 265–266 (DMF) | 80% |
| 38 | $C_2H_5$ | —N\_\_\_O (morpholine) | 258–260 (DMF) | 83% |

EXAMPLE 39

N-Butyl-10-morpholinoethyl-4,10-dihydro-4-oxo-pyrimido[1,2-a]-benzimidazole-3-carboxamide and N-butyl-1-morpholinoethyl-1,4-dihydro-4-oxo-pyrimido[1,2-a]benzimidazole-3-carboxamide By substituting morpholinoethyl chloride for the dimethylaminopropyl chloride in the procedure of Example 6 and subjecting the products, respectively, to the procedure of Examples 7 and 14, N-butyl-10-morpholinoethyl-4,10-dihydro-4-oxo-pyrimido[1,2-a]benzimidazole-3-carboxamide and N-butyl-1-morpholinoethyl-1,4-dihydro-4-oxo-pyrimido[1,2-a]benzimidazole-3-carboxamide, respectively, are obtained.

By following the above procedure of Example 39 and substituting for the morpholinoethyl chloride the indicated aminoalkyl halide and for the butylamine the indicated amine, the following additional products are obtained:

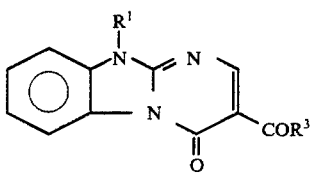
A

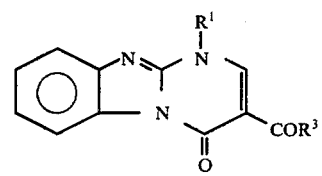
B

| Example | | Aminoalkyl halide | Amine | R¹ | R³ |
|---|---|---|---|---|---|
| 40 | A | ClCH₂N⟨piperidine⟩ | HN(CH₃)₂ | —CH₂N⟨piperidine⟩ | —N(CH₃)₂ |
| | B | ClCH₂N⟨piperidine⟩ | HN(CH₃)₃ | —CH₂N⟨piperidine⟩ | —N(CH₃)₂ |
| 41 | A | Br(CH₂)₂N⟨piperazine⟩NH | H₂NC₂H₅ | —(CH)₂N⟨piperazine⟩NH | —NHC₂H₅ |
| | B | Br(CH₂)₂N⟨piperazine⟩NH | H₂NC₂H₅ | —(CH₂)₂N⟨piperazine⟩NH | —NHC₂H₅ |
| 42 | A | Cl(CH₂)₃N⟨piperazine⟩NCH₂CH₂OH | H₂NC₃H₇ | —(CH₂)₃N⟨piperazine⟩N—CH₂CH₂OH | —NHC₃H₇ |
| | B | Cl(CH₂)₃N⟨piperazine⟩NCH₂CH₂OH | H₂NC₃H₇ | —(CH₂)₃N⟨piperazine⟩NCH₂CH₂OH | —NHC₃H₇ |
| 43 | A | Cl(CH₂)₂N⟨piperazine⟩NCH₃ | H₂NCH₃ | —(CH₂)₂N⟨piperazine⟩NCH₃ | |
| | B | Cl(CH₂)₂N⟨piperazine⟩NCH₃ | H₂NCH₃ | —(CH₂)₂N⟨piperazine⟩NCH₃ | —NHCH₃ |

-continued

| | A | | B | |
|---|---|---|---|---|
| Example | Aminoalkyl halide | Amine | R¹ | R³ |
| 44 | A Cl(CH₂)₂N⟨S⟩ | H₂NC₄H₉ | —(CH₂)₂N⟨S⟩ | —NHC₄H₉ |
| | B Cl(CH₂)₂N⟨S⟩ | H₂NC₄H₉ | —(CH₂)₂N⟨S⟩ | —NHC₄H₉ |

EXAMPLE 45

N-[3-(Dimethylamino)propyl]-1-ethyl-1,4-dihydro-4-oxo-pyrimido[1,2-a]benzimidazole-4-carboxamide By substituting 3-(dimethylamino)propylamine for the n-butylamine in the procedure of Example 14, N-[3-(dimethylamino)-propyl]-1-ethyl-1,4-dihydro-4-oxo-pyrimido[1,2-a]benzimidazole-4-carboxamide is obtained, m.p. 225°–227°.

EXAMPLE 46

1-Benzyl-3-(4-morpholinylcarbonyl)pyrimido[1,2-a]benzimidazole-4(1H)one

By substituting 1-benzyl-1,4-dihydro-4-oxo-pyrimido-[1,2-a]benzimidazole-3-carboxylic acid ethyl ester in part *a* and morpholine in part *b* of Example 33, 1-benzyl-3-(4-morpholinylcarbonyl)pyrimido[1,2-a]benzimidazole-4(1H)one is obtained.

The following additional compounds are obtained by the procedure of Example 33.

| Ex. | R¹ | R² | R³ |
|---|---|---|---|
| 47 | C₂H₅ | —C₂H₅ | —N⟨NH⟩ |
| 48 | CH₃ | CH₃ | —N⟨NCH₂CH₂OH⟩ |
| 49 | CH₃ | —C₂H₅ | —OH |
| 50 | C₂H₅ | H | —N⟨S⟩ |
| 51 | C₂H₅ | H | —N⟨CH₃...CH₃⟩ |
| 52 | CH₃ | CH₃ | —N⟨⟩ |
| 53 | —(CH₂)₂—Ph | CH₃ | —N⟨N—CH₃⟩ |

EXAMPLE 54

10-Ethyl-4,10-dihydro-4-oxo-pyrimido[1,2-a]benzimidazole-3-carboxylic acid, methyl ester and 1-ethyl-1,4-dihydro-4-oxo-pyrimido[1,2-a]benzimidazole-3-carboxylic acid, methyl ester By substituting methoxymethylenemalonic acid dimethyl ester for the ethoxymethylenemalonic acid diethyl ester in the procedure of Example 1, 10-ethyl-4,10-dihydro-4-oxo-pyrimido[1,2-a]benzimidazole-3-carboxylic acid, methyl ester and 1-ethyl-1,4-dihydro-4-oxo-pyrimido[1,2-a]benzimidazole-3-carboxylic acid, methyl ester, respectively, are obtained.

EXAMPLE 55

By substituting the indicated amine for the n-butylamine in the procedures of Examples 7 (product A) or 14 (product B), respectively, the following products are obtained:

| Example | Amine | Compound | $R^1$ | $R^2$ | R |
|---|---|---|---|---|---|
| 56 | $HN(C_3H_7)_2$ | A | $C_2H_5$ | H | $-N(C_3H_7)_2$ |
|  | $HN(C_3H_7)_2$ | B | $C_2H_5$ | H | $-N(C_3H_7)_2$ |
| 57 | $NH_3$ | A | $C_2H_5$ | H | $-NH_2$ |
|  | $NH_3$ | B | $C_2H_5$ | H | $-NH_2$ |
| 58 | $H_2NCH_2-C_6H_5$ | A | $C_2H_5$ | $CH_3$ | $-NHCH_2-C_6H_5$ |
|  | $H_2NCH_2-C_6H_5$ | B | $C_2H_5$ | $CH_3$ | $-NHCH_2-C_6H_5$ |
| 59 | $HN(CH_3)_2$ | A | $CH_3$ | $CH_3$ | $-N(CH_3)_2$ |
|  | $HN(CH_3)_2$ | B | $CH_3$ | $CH_3$ | $-N(CH_3)_2$ |
| 60 | $H_2N-C_6H_4-Cl$ | A | $C_2H_5$ | H | $-NH-C_6H_4-Cl$ |
|  | $H_2N-C_6H_4-Cl$ | B | $C_2H_5$ | H | $-NH-C_6H_4-Cl$ |
| 61 | $H_2N-C_6H_4-Br$ | A | $C_2H_5$ | H | $-NH-C_6H_4-Br$ |
|  | $H_2N-C_6H_4-Br$ | B | $C_2H_5$ | H | $-NH-C_6H_4-Br$ |
| 62 | $H_2N-C_6H_4-CH_3$ | A | $C_2H_5$ | $CH_3$ | $-NH-C_6H_4-CH_3$ |
|  | $H_2N-C_6H_4-CH_3$ | B | $C_2H_5$ | $CH_3$ | $-NH-C_6H_4-CH_3$ |

EXAMPLE 63

10-Benzyl-4,10-dihydro-4-oxo-pyrimido[1,2-a]benzimidazole-3-carboxylic acid

By substituting benzyl bromide for the ethyl iodide in the procedure of Example 1b and then hydrolyzing the product by the procedure of Example 25a, 10-benzyl-4,10-dihydro-4-oxo-pyrimido[1,2-a]benzimidazole-3-carboxylic acid is obtained.

What is claimed is:

1. A compound of the formula

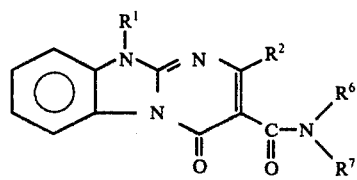

wherein $R^1$ is hydrogen, lower alkyl, phenyl-lower alkyl or

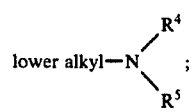

$R^2$ is hydrogen or lower alkyl;

$R^4$ and $R^5$ each is lower alkyl;

$R^6$ and $R^7$ together with the nitrogen form an unsubstituted or substituted pyrrolidino, piperidino, piperazinyl, morpholino or thiamorpholino radical wherein the substituent is hydroxy-lower alkyl or one or two lower alkyl groups;

and physiologically acceptable salts thereof.

2. A compound of the formula

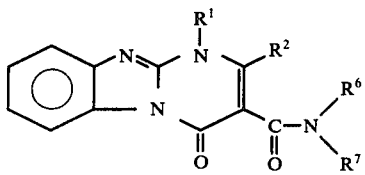

wherein $R^1$, $R^2$, $R^6$ and $R^7$ have the same meaning as in claim 1, and physiologically acceptable salts thereof.

3. A compound as in claim 1 wherein $R^2$ is hydrogen.

4. A compound as in claim 2 wherein $R^2$ is hydrogen.

5. A compound as in claim 1 wherein $R^1$ is lower alkyl; $R^2$ is hydrogen and

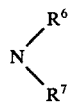

is piperidino, morpholino, piperazino or (lower alkyl)-piperazino.

6. A compound as in claim 2 wherein $R^1$ is lower alkyl; $R^2$ is hydrogen and

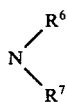

is piperidino, morpholino, piperazino or (lower alkyl)-piperazino.

7. A compound as in claim 3 wherein $R^1$ is ethyl and

is 4-methylpiperazino.

8. A compound as in claim 3 wherein $R^1$ is ethyl and

is piperidino.

9. A compound as in claim 3 wherein $R^1$ is ethyl and

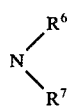

is morpholino.

10. A compound as in claim 4 wherein $R^1$ is ethyl and

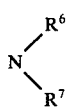

is 4-methylpiperazino.

11. A compound as in claim 4 wherein $R^1$ is ethyl and

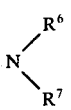

is piperidino.

12. A compound as in claim 4 wherein $R^1$ is methyl and

is morpholino.

* * * * *

UNITED STATES PATENT AND TRADEMARK OFFICE
CERTIFICATE OF CORRECTION

PATENT NO. : 4,109,087
DATED : August 22, 1978
INVENTOR(S) : Theodor Denzel, Hans Hoehn It is certified that error appears in the above-identified patent and that said Letters Patent are hereby corrected as shown below:

Column 11, Example 26b under $R^3$, the formula should read

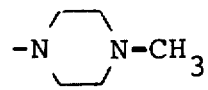

Column 14, Example 42b under $R^3$ should be inserted -- $-NHC_3H_7$ --.
Column 14, Example 43a under $R^3$ should be inserted -- $-NHCH_3$.

Signed and Sealed this

Thirtieth Day of October 1979

[SEAL]

Attest:

RUTH C. MASON
Attesting Officer

LUTRELLE F. PARKER
Acting Commissioner of Patents and Trademarks